(12) United States Patent
Couch et al.

(10) Patent No.: US 6,913,768 B2
(45) Date of Patent: Jul. 5, 2005

(54) SUSTAINED RELEASE DELIVERY OF AMPHETAMINE SALTS

(75) Inventors: Richard A. Couch, Bryn Mawr, PA (US); Beth A. Burnside, Bethesda, MD (US); Rong-Kun Chang, Rockville, MD (US)

(73) Assignee: Shire Laboratories, Inc., Rockville, MD (US)

( * ) Notice: Subject to any disclaimer, the term of this patent is extended or adjusted under 35 U.S.C. 154(b) by 115 days.

(21) Appl. No.: 10/353,073

(22) Filed: Jan. 29, 2003

(65) Prior Publication Data

US 2004/0059002 A1 Mar. 25, 2004

Related U.S. Application Data

(60) Provisional application No. 60/412,799, filed on Sep. 24, 2002.

(51) Int. Cl.⁷ .............................. A61K 9/16; A61K 9/20; A61K 9/22; A61K 9/48; A61K 9/14
(52) U.S. Cl. ...................... 424/490; 424/489; 424/494; 424/495; 424/484; 424/486; 424/464; 424/468; 424/451; 424/457
(58) Field of Search ................................ 424/490, 489, 424/494, 495, 484, 486, 464, 468, 451, 457

(56) References Cited

U.S. PATENT DOCUMENTS

| | | | |
|---|---|---|---|
| 4,049,791 A | * | 9/1977 | Cohen |
| 4,723,958 A | | 2/1988 | Pope et al. |
| 4,728,512 A | | 3/1988 | Mehta et al. |
| 4,765,989 A | | 8/1988 | Wong et al. |
| 4,871,549 A | | 10/1989 | Ueda et al. |
| 4,891,230 A | | 1/1990 | Geoghegan et al. |
| 4,894,240 A | | 1/1990 | Geoghegan et al. |
| 4,902,516 A | | 2/1990 | Korsatko et al. |
| 4,917,899 A | | 4/1990 | Geoghegan et al. |
| 5,002,776 A | | 3/1991 | Geoghegan et al. |
| 5,011,692 A | | 4/1991 | Fujioka et al. |
| 5,011,694 A | | 4/1991 | Nuernberg et al. |
| 5,051,262 A | | 9/1991 | Panoz et al. |
| 5,093,200 A | | 3/1992 | Watanabe et al. |
| 5,156,850 A | | 10/1992 | Wong et al. |

(Continued)

FOREIGN PATENT DOCUMENTS

| | | |
|---|---|---|
| EP | 0 212 747 | 3/1987 |
| GB | 768 512 A | 2/1957 |
| WO | WO 87/00044 | 1/1987 |
| WO | WO 90/09168 | 8/1990 |
| WO | WO 97/03672 | 2/1997 |

(Continued)

OTHER PUBLICATIONS

US 6,034,101, 3/2000, Gupta et al. (withdrawn)
Walia et al., Preliminary Evaluation of an Aqueous Wax, Emulsion for Controlled–Release Coating, Pharm. Dev. Tech., vol. 3, No. 1, pp. 103–113 (1998).
Banker et al., Modern Pharmaceutics, eds., Marcel Dekker, Inc., New York, p. 350 (1996).

(Continued)

*Primary Examiner*—Thurman K. Page
*Assistant Examiner*—Humera N. Sheikh
(74) *Attorney, Agent, or Firm*—Millen, White, Zelano, Branigan, P.C.

(57) ABSTRACT

A pharmaceutical composition comprises a once-a-day sustained release formulation of at least one amphetamine salt which provides mean plasma concentration profile aspects in human ADHD patients which are substantially the same as that provided by ADDERALL XR® type pulsatile formulations.

37 Claims, 13 Drawing Sheets

U.S. PATENT DOCUMENTS

| | | |
|---|---|---|
| 5,226,902 A | 7/1993 | Bae et al. |
| 5,229,131 A | 7/1993 | Amidon et al. |
| 5,232,705 A | 8/1993 | Wong et al. |
| 5,260,068 A | 11/1993 | Chen |
| 5,260,069 A | 11/1993 | Chen |
| 5,275,819 A | 1/1994 | Amer et al. |
| 5,308,348 A | 5/1994 | Balaban et al. |
| 5,312,388 A | 5/1994 | Wong et al. |
| 5,364,620 A | 11/1994 | Geoghegan et al. |
| 5,395,628 A | 3/1995 | Noda et al. |
| 5,407,686 A | 4/1995 | Patel et al. |
| 5,474,786 A | 12/1995 | Kotwal et al. |
| 5,496,561 A | 3/1996 | Okada et al. |
| 5,616,345 A | 4/1997 | Geoghegan et al. |
| 5,800,836 A | 9/1998 | Morella et al. |
| 5,824,341 A | 10/1998 | Segh et al. |
| 5,824,342 A | 10/1998 | Cherukuri et al. |
| 5,824,343 A | 10/1998 | Na et al. |
| 5,837,284 A * | 11/1998 | Mehta et al. |
| 5,840,329 A | 11/1998 | Bai |
| 5,885,616 A | 3/1999 | Hsiao et al. |
| 5,885,998 A | 3/1999 | Bencherif et al. |
| 5,891,474 A | 4/1999 | Busetti et al. |
| 5,908,850 A | 6/1999 | Zeitlin et al. |
| 5,922,736 A | 7/1999 | Dariani et al. |
| 5,945,123 A | 8/1999 | Hermelin |
| 6,183,780 B1 | 2/2001 | Van Balken et al. |
| 6,214,379 B1 | 4/2001 | Hermelin |
| 6,217,904 B1 * | 4/2001 | Midha et al. |
| 6,228,398 B1 | 5/2001 | Devane et al. |
| 6,322,819 B1 | 11/2001 | Burnside et al. |
| 6,340,476 B1 | 1/2002 | Midha et al. |
| 6,605,300 B1 | 8/2003 | Burnside et al. |

FOREIGN PATENT DOCUMENTS

| | | |
|---|---|---|
| WO | WO 99/30694 | 6/1999 |
| WO | WO 99/51209 | 10/1999 |
| WO | WO 00/23055 | 4/2000 |
| WO | WO 00/35426 | 6/2000 |
| WO | WO 00/35450 | 6/2000 |
| WO | WO 0059481 | 10/2000 |

OTHER PUBLICATIONS

Gazzaniga et al., "Time–Dependent oral Delivery Systems for Colon Targeting," S.T.P. Pharma Sciences 5(1):83–88 (1995).

Walia et al., "Preliminary Evaluation of An Aqueous Wax Emulsion for Controlled–Release Coating," Pharmaceutical Development and Technology, 3(1):103–113 (1998).

Gazzaniga et al., "Oral Chronotopic Drug Delivery Systems: Achievement of Time And/Or Site Specificity," Eur. J. Pharm. Biopharm, 40(4):246–250 (1994).

Pozzi et al., "The Time Clock System: A New Oral Dosage form for Fast and Complete release od Drug After a Predetermined Lag Time," Journal of Controlled Release, 31:99–108 (1994).

Wilding et al., "Gastrointestinal Transit and Systemic Absorption of Captopril From A Pulsed–Release Formulation," Pharmaceutical Research, 9 (5):654–657(1992).

Xin Xu et al., "Programmable Drug Delivery From An Erodible Association Polymer System," Pharmaceutical Research, 10(8):1144–1152 (1993).

Conte et al., "Press–Coated tablets for Time–Programmed Release of Drugs," Biomaterials, 14(13):1017–1023 (1993).

R. Gurny et al., Pulsatile Drug Delivery Current Applications and Future Trends, pp. 112–134, (1993).

Adderall XR, Package Insert, Oct. 2001.

Dexedrine, Spansule Capsules, Package Insert, Physicians' Desk Reference 1997.

Adderall, Package Insert, May 1996, Physicians' Desk Reference 1997.

K. S. Patrick et al., "Pharmacology of Methylphenidate, Amphetamine Enantiomers and Pemoline in Attention–Deficit . . . " Human Psychopharmacology, vol. 12, pp. 527–546, 1997.

Lisa H. Brauer et al., "Acute Tolerance to Subjective but Not Cardiovascular Effects of d–Amphetamine in Normal, Healthy Men," Journal of Clinical Psychopharmacology, vol. 16, No. 1, pp. 72–76, 1996.

William P. Melega et al., "Pharmacokinetic and Pharmacodynamic Analysis of the Actions of D–Amphetamine and D–Methamphetamine on the Dopamine Terminal," The Journal of Pharmacology and Experimental Therapeutics, vol., 274, No. 1, pp, 90–96, 1995.

Peter Clausing et al., "Amphetamine Levels in Brain Microdialysate, Caudate/Putamen, Substantia Nigra and Plasma After Dosage That Produces Either Behavioral . . . " The Journal of Pharmacology and Experimental Therapeutics, vol. 274, No. 2, pp. 614–621, 1995.

S.B. Sparber et al., "Amphetamine Cumulation and Tolerance Development: Concurrent and Opposing Phenomena," Pharmacology Biochemistry & Behavior, vol. 20, pp, 415–424, 1984.

Burt Angrist et al., "Early Pharmacokinetics and Clinical Effects of Oral D–Amphetamine in Normal Subjects," Biol Psychiatry, vol. 22, pp. 1357–1368, 1987..

Gerald L. Brown et al., Plasma Levels of d–Amphetamine in Hyperactive Children, PSYCHOPHARMACOLOGY, vol. 62, pp. 133–140, 1979.

Suk Han Wan et al., "Kinetics, Salivary Excretion of Amphetamine Isomers, and Effect of Urinary pH," Clin. Pharmacol. Ther., pp. 585–590, May 1978.

Gerald L. Brown et al., "Plasma d–Amphetamine Absorption and Elimination in Hyperactive Children," Psychopharmacology Bulletin, vol. 14, No. 3, pp. 33–35, 1978.

Excerpts from Feb. 2, 2005 Deposition of Beth A. Burnside in *Shire Laboratories Inc v Barr Laboratories, Inc.*, 03–CV–1219 and 03–CV–6632 (PKC), SDNY, pp. 1, 2 and 143–150.

Excerpts from Feb. 3, 2005 Deposition of Beth A Burnside in *Shire Laboratories Inc v Impax Laboratories Inc*, 03–CV–1164 (GMS), D.Delaware, pp. 1–5 and 190–197.

* cited by examiner

Figure 2. Mean CGIS-P total scores for ITT population.

- *Baseline (previous med)

Week 1 (Adderall XR™)
Week 3 (Adderall XR™)
Week 7 (Adderall XR™)

8-h CGIS-P (N=2911)   12-h CGIS-P (N=2909)

*P<0.0001 vs baseline. Note: a lower score indicates better response to treatment Figure 3. CGI Improvement scores at week 7.

Figure 5. Parent Satisfaction Survey:
"Overall, I am satisfied with my child taking this medication."

Figure 6. Physician Preference Survey:
"Overall, which of the two medications do you prefer?"

Figure 13. Visit schedule and monitoring.

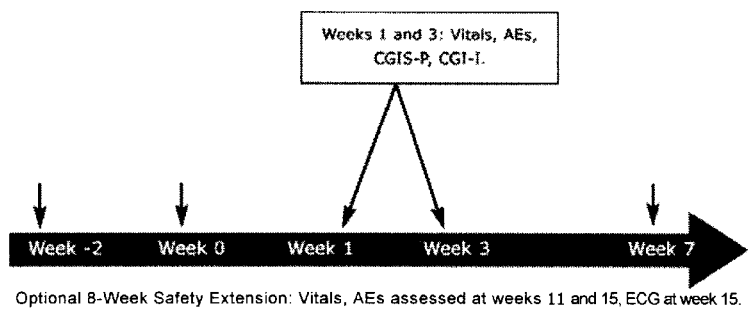

Optional 8-Week Safety Extension: Vitals, AEs assessed at weeks 11 and 15, ECG at week 15.

Treatment: Adderall XR™ was initiated the day after the baseline visit according to the dose conversion paradigm outlined in Table 1. The dose could be increased as clinically warranted based on the CGI and CGIS-P; decrease in dose was allowed based on safety/tolerability.

SUSTAINED RELEASE DELIVERY OF AMPHETAMINE SALTS

This application claims the benefit of U.S. application Ser. No. 60/412,799 filed on Sep. 24, 2002.

Described herein are compositions for providing an orally administrable sustained release (SR) form of one or more amphetamines and/or amphetamine salts. Also described are methods for administering the sustained release form of one or more amphetamine salts to a patient in need thereof. Preferably, the methods are carried out for treatment of patients having ADHD (attention deficit hyperactivity disorder), but other disease states can also be treated. The sustained-release forms of one or more amphetamines and/or amphetamine salts according to the invention are preferably formulated to provide an in vivo plasma concentration profile (i.e., measured by total concentration of the amphetamines and/or amphetamine salts (often with separate tracking of d-and l-isomers) in the patients' blood plasma) which is substantially equivalent to the in vivo plasma concentration profile achieved by pulsatile release formulations of the same amphetamines and/or amphetamine salts when administered to a patient, e.g., those achieved by ADDERALL XR®, Shire US Inc., whose FDA package insert and labeling are entirely incorporated by reference herein. Further preferably, this sustained release profile (the plasma concentration profile being distinguished from the release profile) typically exhibits first order or biphasic or sigmoidal characteristics.

Particularly preferably, the SR formulations according to the invention exhibit a single dose in vivo plasma concentration profile substantially the same as that shown in FIG. 1. The latter shows the substantially smooth mean (over about 20 patients) plasma concentration curves achieved for both the dextroamphetamine and levoamphetamine salts in ADDERALL XR®. (The overall mean plasma concentration curve for total amphetamine level is simply the sum of the two curves shown in FIG. 1). Because the formulations of this invention achieve substantially the same mean plasma concentration curves, they can be termed fast sustained release formulations, with regard to the initial rising slopes involved.

By substantially the same "profile" herein is meant that two curves have substantially the same AUC (area under the curve) and $C_{max}$, e.g., these parameters for each curve are ±20% of each other, or even closer, e.g. ±10%, ±5%, ±2%, etc., which parameters are entirely conventionally defined and determined. See, e.g., *Fundamentals of Clinical Pharmacokinetics*. J. G. Wagner, Drug Intelligence Publications, Inc., Hamilton, Ill., 1975; *Guidance for Industry, Bioavailability and Bioequivalence Studies for Orally Administered Drug Products-General Considerations, FDA, CDER*. October 2000. For FIG. 1, AUC (time zero to infinity) is 556.6 ng hr/mL and $C_{max}$ is 28.0 ng/mL for d-amphetamine and 205.1 ng hr/mL and 8.7 ng/mL, respectively, for 1-amphetamine. Of course, plasma curves achieved by this invention can follow even more closely the course of a target curve such as that shown in FIG. 1, e.g., substantially (e.g, ±20%) matching initial rising slope, post-peak curve shapes, $T_{max}$ values, (7.1 hr for d-amphetamine and 7.4 hr for 1-amphetamine for FIG. 1), etc. Whereas FIG. 1 shows data for 20 mg tablets (i.e., two 10 mg pulsatile doses), the plasma curves (and e.g., AUC and $C_{max}$) corresponding to other daily doses such as 10, 30, 40, 50, 60, 70, 80, 90 mg will be essentially linearly proportional to those shown in FIG. 1, corresponding to the involved dosage.

In another independent embodiment, the fast SR formulations of this invention, for the ADDERALL X® 20 mg dose of FIG. 1, exhibit plasma concentration curves having initial (e.g., from 2 hours after administration to 4 hours after administration) slopes of about 3.7 to about 11.4 ng/(mL hr) for dextroamphetamines and about 1.4 to about 3 ng/(mL hr) for levoamphetamines, preferably, about 4 to about 8 ng/(mL hr) and about 1.5 to about 2.2 ng/(mL hr), respectively. The precise slope for a given individual will vary according to usual factors, including whether the patient has eaten or not. For other doses, e.g., those mentioned above, the slopes vary directly (linearly) proportionally to dose.

The formulations of WO 00/23055 (whose entire disclosure is incorporated by reference herein), e.g., that for ADDERALL X®, achieve a two-fold release of active amphetamine salts, one an immediate release dosage form and the other a delayed release dosage form. Typically, the lag time between the immediate release (release upon administration) and delayed release forms is 2–6 hours, preferably about 3 to about 5 hours, more preferably about 3 to about 4 hours, and typically about four hours. In one embodiment, the fast sustained release formulations of this invention are used to provide a mean plasma concentration profile substantially the same as that of Example 5 (combination of Examples 1 and 2) of WO 00/23055, despite the latter's disclosure that conventional sustained release formulation technology was not suitable for amphetamines. (Note that the plasma profile of Example 5 shown in FIG. 7 of WO 00/23055 is not a mean profile, as is that of FIG. 1 of this application, but rather is one from a single individual.)

The SR formulations of this invention will be effective to treat, e.g., ADHD, in the same manner as ADDERALL® XR. For example, they will be effective to treat ADHD in the unexpectedly good manner established in the data reported in Example 10. They will also be effective to treat ADHD with low incidence of side effects, including substance abuse, addiction, tolerance, tachyphylaxis, etc.

Preferred salts are those in the commercial product ADDERALL XR®, i.e., dextroamphetamine sulfate, dextroamphetamine saccharate, amphetamine aspartate monohydrate and amphetamine sulfate. However, the invention is not limited to these specific amphetamine salts. Other amphetamines and amphetamine salts and mixtures thereof can be used in a sustained-release delivery system to achieve the plasma concentration profiles of the invention. For example, amphetamine base, chemical and chiral derivatives thereof and other amphetamine salts can be used.

Preferred in vivo plasma concentration profiles of the amphetamine salts can be accomplished by providing a solid dosage form of the amphetamine salts which is capable of providing a sustained release of the one or more amphetamine salts over a time period of, for example, from 8–12 hours, or longer, preferably, 10–12 hours. For example, the amphetamine salts can be provided in a core which is coated with a coating which allows the release of the amphetamine salts there through over time, such as a pharmaceutically acceptable water-insoluble film former alone or with a dissolution regulating agent. In addition, by combining the immediate-release beads with the sustained-release beads, a biphasic release profile can be achieved. Other methods for providing sustained-release of a drug, including those further discussed below, are known and can be used to provide a sustained-release delivery which results in the above-discussed in vivo plasma concentration profile.

Suitable sustained-release systems, include SR coatings, e.g., on beads, SR matrices (i.e., no coatings needed), SR osmotic systems, etc. whereby amphetamine salts achieve a first order, biphasic, sigmoidal etc. release profile to achieve the plasma profile equivalent of pulsatile release systems of the same drugs as discussed above. Matching to the desired target plasma concentration profile using SR is conventional.

Sustained-release beads can be prepared by coating conventional drug-containing cores with a water-insoluble polymer, or a combination of water-insoluble polymers, or a combination of water-insoluble and water-soluble polymers. This is usually not a combination of layers, but a combination of polymers in a single coating. The resultant beads (or tiny tablets) can then be placed in a capsule. Other than beads in a capsule shell, tablets in a capsule shell (e.g., one immediate-release tablet and one delayed, sustained release tablet in a capsule shell, to provide an overall sustained release) also can be used to attain the desired plasma profile.

Various polymeric materials can be used to achieve the type of pattern of release needed to result in the desired plasma concentration profile, for example, so as to increase the fast rate of delivery over the first 4 to 8 hours of delivery. For example, a multiple dosage form (e.g., as discussed below) of the present invention can deliver rapid and complete dosages of pharmaceutically active amphetamine salts to achieve the desired plasma profile of the drug in a recipient over the course of about 8–12 hours with a single oral administration. In so doing, the levels of drug in blood plasma of the pharmaceutically active amphetamine salts will reach a peak fairly rapidly, for example, over the course of about 8 hours or less as desired, which then slowly decreases over the course of, for example, the next 12 or more hours. The desired plasma concentration profile can thus be achieved using a fast sustained-release once daily dosage of the amphetamine salts.

Examples of useful bead constructions for sustained-release include the following:

Sugar core, coated with amphetamine, coated with polymer,

Sugar core, coated with amphetamine, coated with mix of amphetamine and polymer, coated with polymer, Sugar core, coated with amphetamine, coated with relatively high concentration mix of amphetamine and polymer, coated with weaker concentration mix of amphetamine and polymer, coated with polymer, Bead containing amphetamine, coated with polymer, Bead containing amphetamine, coated with mix of amphetamine and polymer, coated with polymer, Bead containing amphetamine, coated with relatively high concentration mix of amphetamine and polymer, coated with weaker concentration mix of amphetamine and polymer, coated with polymer, and Tablet or capsule containing multiple types of beads as described above having differing timing of release of amphetamine and/or different rates of release of amphetamine.

As mentioned, SR matrix beads can also be used, i.e., not having any needed layers to achieve sustained release. The components used in such matrices are chosen from conventional SR polymers. In another construct, there can be included in the formulation, along with the layered beads or matrix beads, immediate release formulations which provide one way to achieve a desired initial fast release. Such immediate release formulations are fully conventional. See e.g., WO 00/23055.

Details of using the foregoing constructs and others to achieve a desired plasma profile as discussed above are fully conventional and can be determined by those of skill in the art with at most a few routine parametric experiments, and conventional adjustments. e.g., involving identities of polymers and mixtures thereof, relative amounts of components, coating thicknesses, bead diameters, number of layers and compositions thereof, etc. Thus, for example, for a given construct (e.g., one of those in the examples herein), dissolution profiles can be determined and in vivo plasma profiles measured. The latter can then conventionally be compared to the target plasma profile (e.g., that of ADDERALL XR®) and differences compensated by fully conventional formulation and dissolution profile adjustments such as but not limited to those mentioned.

Suitable materials which can be used in the SR formulations of this invention are well known and include but are not limited to polyvinyl acetate, cellulose acetate, cellulose acetate butyrate, cellulose acetate propionate, ethyl cellulose, fatty acids and their esters, alkyl alcohols, waxes, zein (prolamine from corn), and aqueous polymeric dispersions such as Eudragit® RS and RL30D, Eudragit® NE30D, Aquacoat®, Surelease®, Kollicoat® SR30D, and cellulose acetate latex.

Methods of manufacturing cores include:

a. Extrusion-Spheronization—the drug(s) and other additives are granulated with the addition of a binder solution. The wet mass is passed through an extruder equipped with a certain size screen. The extrudates are spheronized in a marumerizer. The resulting pellets are dried and sieved for further applications.

b. High-Shear Granulation—Drug(s) and other additives are dry-mixed and then the mixture is wetted by addition of a binder solution in a high shear-granulator/mixer. The granules are kneaded after wetting by the combined action of mixing and milling. The resulting granules or pellets are dried and sieved for further applications.

c. Solution or Suspension Layering—A drug(s) solution or dispersion with or without a binder is sprayed onto starting seeds with a certain particle size in a fluidized bed processor or other suitable equipment. The drug thus is coated on the surface of the starting seeds. The drug-loaded pellets are dried for further applications.

For purposes of the present invention, the core particles, preferably, have a diameter in the range of about 500–1500 microns (micrometers); more preferably 100–800 microns. These particles can then be coated in a fluidized bed apparatus with an alternating sequence of selected coating layers.

The composition, preferably in the bead forms described above, can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. A lubricant can further be added if necessary by using, for example, polyethylene glycol, leucine, glyceryl behenate, magnesium stearate or calcium stearate.

The composition may also be incorporated into a tablet, in particular by incorporation into a tablet matrix, which rapidly disperses the particles after ingestion. In order to incorporate these particles into such a tablet, a filler/binder must be added to a tablet that can accept the particles, but will not allow their destruction during the tableting process. Materials that are suitable for this purpose include, but are not limited to, microcrystalline cellulose (AVICEL®). soy polysaccharide (EMCOSOY®), pre-gelatinized starches (STARCH® 1500, NATIONAL® 1551), and polyethylene glycols (CARBOWAX®). The materials are preferably present in the range of 5–75% (w/w), with a more preferred range of 25–50% (w/w).

In addition, disintegrants are optionally added in order to disperse the beads once the tablet is ingested. Suitable disintegrants include, but are not limited to: cross-linked sodium carboxymethyl cellulose (AC-DI-SOL®), sodium starch glycolate (EXPLOTAB®, PRIMOJEL®), and cross-linked polyvinylpolypyrrolidine (Plasone-XL). These materials are preferably present in the rate of 3–15% (w/w), with a more preferred range of 5–10% (w/w).

Lubricants are also optionally added to assure proper tableting, and these can include, but are not limited to: magnesium stearate, calcium stearate, stearic acid, polyethylene glycol, leucine, glyceryl behanate, and hydrogenated vegetable oil. These lubricants are preferably present in amounts from 0.1–10% (w/w), with a more preferred range of 0.3–3.0% (w/w).

Tablets are formed, for example, as follows. The particles are introduce into a blender along with AVICEL®, disintegrants and lubricant, mixed for a set number of minutes to provide a homogeneous blend which is then put in the hopper of a tablet press with which tablets are compressed. The compression force used is adequate to form a tablet; however, not enough to fracture the beads or coatings.

Various enteric materials, e.g., cellulose acetate phthalate, hydroxypropyl methylcellulose phthalate, polyvinyl acetate phthalate, and the EUDRAGIT® acrylic polymers, can be used as gastroresistant, enterosoluble coatings for drug release in the intestine when desired. The enteric materials, which are soluble at higher pH values, are frequently used for colon-specific delivery systems and are entirely conventionally employable in the SR systems of this invention. The enteric polymers used in this invention can also be modified conventionally by mixing with other known coating products that are not pH sensitive. Examples of such coating products include the neutral methacrylic acid esters with a small portion of trimethylammonioethyl methacrylate chloride, sold currently under the trade names EUDRAGIT® and EUDRAGIT® RL; a neutral ester dispersion without any functional groups, sold under the trade names EUDRAGIT® NE30D and EUDRAGIT® NE30; another pH independent coating products.

A conventional protective coating layer may also be applied immediately outside the core, either a drug-containing matrix core or a drug-layered core, by conventional coating techniques such as pan coating or fluid bed coating using solutions of polymers in water or suitable organic solvents or by using aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions (AQUACOAT®, SURELEASE®), EUDRAGIT® RL30D, OPADRY® and the like. The suggested coating levels are from 1 to 6%, preferably 2–4% (w/w).

An overcoating layer can further optionally be applied to the composition of the present invention. OPADRY®, OPADRYII® (Colorcon) and corresponding color and colorless grades from Colorcon can be used to protect the pellets from being tacky and provide colors to the product. The suggested levels of protective or color coating are from 1 to 6%, preferably 2–3% (w/w).

Many ingredients can be incorporated into the overcoating formula, for example to provide a quicker (immediate) release, such as plasticizers: acetyltriethyl citrate, triethyl citrate, acetyltributyl citrate, dibutylsebacate, triacetin, polyethylene glycols, propylene glycol and the others; lubricants: talc, colloidal silica dioxide, magnesium stearate, calcium stearate, titanium dioxide, magnesium silicate, and the like.

Optionally modifying components of a protective layer which can be use over the enteric or other coatings include a water penetration barrier layer (semi-permeable polymer) which can be successively coated after the enteric or other coating to reduce the water penetration rate through the enteric coating layer and thus increase the lag time of the drug release. Sustained-release coatings commonly known to one skilled in the art can be used for this purpose by conventional coating techniques such as pan coating or fluid bed coating using solutions of polymers in water or suitable organic solvents or by using aqueous polymer dispersions. For example, the following materials can be used, but not limited to: cellulose acetate, cellulose acetate butyrate, cellulose acetate propionate, ethyl cellulose, fatty acids and their esters, waxes, zein, and aqueous polymer dispersions such as EUDRAGIT® RS and RL 30D, EUDRAGIT® NE 30D, AQUACOAT®, SURELEASE®, cellulose acetate latex. The combination of the above polymers and hydrophilic polymers such as hydroxyethyl cellulose, hydroxypropyl cellulose (KLUCEL®, Hercules Corp.), hydroxypropyl methylcellulose (METHOCEL®, Dow Chemical Corp.), polyvinylpyrrolidone can also be used.

Principles of sustained release formulation technology applicable to this invention, including the exemplary modes mentioned herein, are disclosed, e.g., in R. K. Chang and J. R. Robinson, chapter 4: "Sustained Drug Release from Tablets and Particles Through Coating," in *Pharmaceutical Dosage Forms: Tablets,* volume 3, edited by H. A. Lieberman, L. Lachman, and J. B. Schwartz, Marcel Dekker, Inc., 1991; R. J. Campbell and G. L. Sackett, chapter 3: "Film coating," in *Pharmaceutical Unit Operations: Coating,* edited by K. E. Avis, A. J. Shukla, and R. K. Chang, Interpharm Press, Inc., 1999, whose disclosures are entirely incorporated by reference herein.

This invention also relates to use of the SR formulations to treat indications other than ADHD at dosages and in regimens analogous to those described herein. These include but are not limited to Alzheimer's disease and other memory disorders, fibromyalgia, chronic fatigue, depression, obsessive compulsive disorder, alone or in combination with a SSRI; oppositional defiant disorder (ODD), with or without ADHD and with or without guanfacine or welbutrin; anxiety, with or without ADHD and alone or in combination with an anxiolytic or SSRI; resistant depression; stroke rehabilitation; Parkinson's disease; mood disorder; schizophrenia; Huntington's disorder; dementia, e.g. AIDS dementia and frontal lobe dementia; movement disfunction; apathy; fatigue; Pick's disease; sleep disorders, e.g., narcolepsy, cataplexy, sleep paralysis and hypnagogic hallucinations; etc.

The invention also relates to combinations of the SR formulations of this invention with other therapeutic agents, including all those useful for a given indication. The involved drugs can be formulated in the same dosage form as the SR dose of this invention or can be formulated separately, e.g., as conventionally used alone, in which case, the drugs can be administered sequentially in any order or simultaneously. Typically, dosages can be in the same ranges as for each drug used separately or, where synergistic effects occur, one or more of the combined drugs can be used in lower dosages. Combinations encompass any where the drugs are made bioavailable in a patient at the same time, including combinations coming into being in a patient.

These other therapeutic agents include e.g., for Alzheimer's: Reminyl, Cognex, Aricept, Exelon, Akatinol, Neotropin, Eldepryl, Estrogen, Clioquinol, Ibuprofen, and Ginko Bilboa; for ADHD: methylphenidate (e.g., Ritalin), Dexedrine, Adderall, Cylert, clonidine, guanfacine, etc; for depression: Prozac, Zoloft, Paxil, Reboxetine, Wellbutrin, Olanzapine, Fluoxetine, Elavil, Totranil, Pamelor, Nardil, Parnate, Desyrel, and Effexor; for mood disorder: Thorazine, Haldol, Navane, Mellaril, Clozaril, Risperdal, Zyprexa, Clozapine, Risperidone, and Olanzapine; for fatigue: benzodiazapines, Anaprox, Naprosen, Prozac, Zoloft, Paxil, Effexor, and Desyrel; for fibromyalgia: Dilantin, Carbatrol, Epitol, Tegretol, Depacon, Depakote, Norpramin, Aventyl, Pamelor, Elavil, Enovil, Adapin, Sinequan, Zonalon, and non-steroidal inflammatory drugs; for oppositional defiant disorder (ODD): clonidine, Risperidone, and Zyprexa; for apathy: Amisulpride, Olanzapine, Visperidone, Quetiapine, Clozapine, and Zotepine; for Parkinson's disease: Levodopa, Parlodel, Permax, and MIRAPEX; for schizophrenia: Clozapine, Zyprexa, Seroquel, and Risperdal; for Huntington's disorder: haloperidal and clonzepam; for dementia: thioridazine, haloperidal, Risperidone, Cognex, Aricept, and Exelon; for narcolepsy: Provigil, Dexedrine, Modafinil and Ritalin; for cataplexy: Xyrem; for hallucinations: Clozapine, Risperidone, Zyprexa, and Seroquel; for sleep paralysis: Perocet, Vicodin, and Lorcet; for obsessive compulsive disorder: Anafranil, Prozac, Zoloft, Paxil, Luvox; and for anxiety: Elavil, Asendin, Wellbutrin, Tegretol, Anafranil, Norpramine, Adapin, Sinequan, Tofranil, Epitol, Janimire, Pamelor, Ventyl, Aventyl, Surmontil etc; selective serotonin reuptake inhibitors (SSRIs) including Prozac, Luvox, Serzone, Paxil, Zoloft, Effexor, etc., benzodiazepines, including Xanax, Librium, Klonopin, Valium, Zetran, Valrelease, Dalmane, Ativan, Alzapam, Serax, Halcion, etc., monamine oxidase inhibitors including Aurorix, Manerix, Nardil, Parnate, etc.

The entire disclosures of all applications, patents and publications, cited above, and below, are hereby incorporated by reference.

The following is a brief description of the figures:

FIG. 13 shows a visit schedule and monitoring.

EXAMPLES

Figure 1:
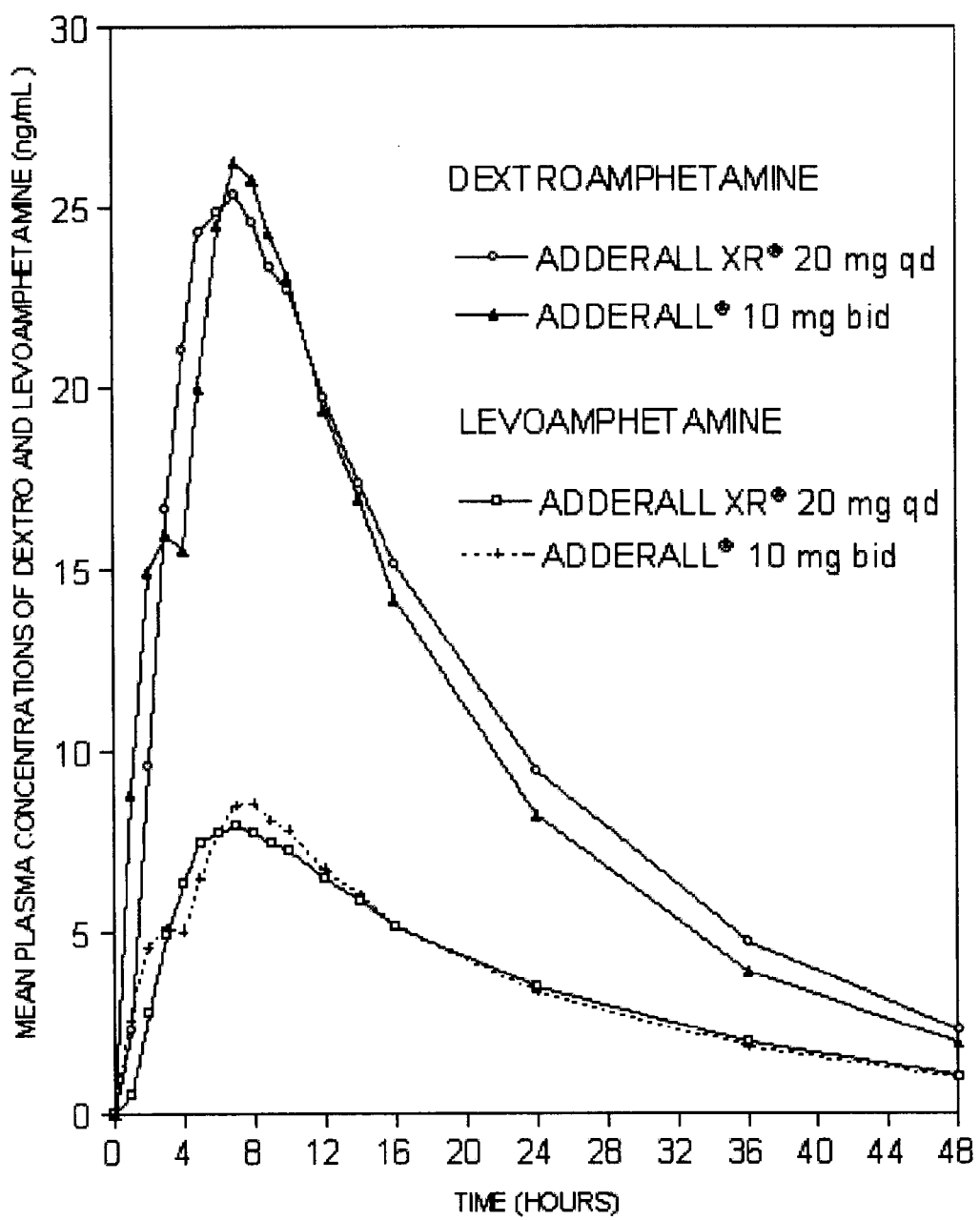
FIG. 1 shows the mean plasma concentration curves for Adderall® and Adderall XR®.

In the foregoing and in the following examples, all temperatures are set forth uncorrected in degrees Celsius; and, unless otherwise indicated, all parts and percentages are by weight.

SR Coated Beads

Example 1

| | |
|---|---|
| Mixed amphetamine salts loaded beads (MASL) | 500 grams |
| Ethyl cellulose (Ethocel N-10, Dow Chemical) | 15.46 grams |
| Ethyl acetate | 515 grams |

Ethyl cellulose (15.46 gram) is dissolved in 515 grams of ethyl acetate. Into a Wurster column is charged 500 grams of MASL beads which are then coated with the coating mixture under conditions of 40° C., spray pressure 1 bar, and spray rate of 10 grams/min. The line is rinsed with ethyl acetate and the pellets are dried for approximately twenty minutes and recovered to give a product of 97% by weight MASL beads and 3% by weight ethyl cellulose coating.

Example 2

| | |
|---|---|
| Mixed amphetamine salts loaded beads | 500 grams |
| Ethyl cellulose (Ethocel N-10, Dow Chemical) | 37.78 grams |
| Hydroxypropyl cellulose (Klucel LF, Aqualon) | 8.70 grams |
| Methylene chloride | 744 grams |
| Methanol | 186 grams |

Ethyl cellulose (37.78 grams) and hydroxypropyl cellulose (8.70 grams) are dissolved in a mixture of methylene chloride and methanol (4:1). Into a Wurster column is charged 500 grams of MASL beads which are then coated with the coating mixture under conditions of 40° C., spray pressure 1 bar, and spray rate 10 grams/min. The line is rinsed with methanol and the pellets are dried for approximately twenty minutes and recovered to give a product of 92% by weight MASL beads and 8% by weight ethyl cellulose/hydroxypropyl cellulose coating.

Example 3

| | |
|---|---|
| Mixed amphetamine salts loaded beads | 500 grams |
| Surelease (Ethyl cellulose-based dispersion, Colorcon) | 173.92 grams |
| Water | 43.48 grams |

Surelease (173.92 grams) is diluted with 43.48 grams of water. Into a Wurster column (Versa-Glatt. Glatt Air Techniques) is charged 500 grams of MASL beads which are then coated with the coating mixture under conditions of 60° C. inlet temperature, spray pressure 1 bar, and spray rate 6 grams/min. The line is rinsed with water and the pellets are dried for approximately twenty minutes and recovered to give a product of 92% by weight MASL beads and 8% by weight ethyl cellulose coating.

Example 4

| | |
|---|---|
| Mixed amphetamine salts loaded beads | 500 grams |
| Eudragit RS30D | 111.49 grams |
| Triethyl citrate | 10.03 grams |
| Water | 115.94 grams |

Triethyl citrate is mixed into Eudragit RS30D for 30 min. The plasticized Eudragit RS30D is diluted with water and filtered through a 60-mesh screen. Into a Wurster column is charged 500 grams of MASL beads which are then coated with the coating mixture under conditions of 40° C. inlet temperature, spray pressure 1 bar, and spray rate 6 grams/min. The line is rinsed with ethyl acetate and the pellets are dried for approximately twenty minutes and recovered to give a product of 92% by weight MASL beads and 8% by weight Eudragit RS30D coating.

Example 5

| | |
|---|---|
| Mixed amphetamine salts loaded beads | 500 grams |
| Mixed amphetamine salts | 48.5 grams |
| Glyceryl behenate (Compritol 888, Gattefosse) | 436.5 grams |

Mixed amphetamine salts are dispersed in the molten glyceryl behenate. The drug-containing hot melt is sprayed onto the mixed amphetamine salts loaded beads in a Wurster column under conditions of 30° C. inlet temperature, spray pressure 2 bar, and a spray rate of 10 grams/min.

Example 6

| | |
|---|---|
| Mixed amphetamine salts loaded beads | 500 grams |
| Eudragit L100 | 25.25 grams |
| Ethyl cellulose (Ethocel N-10, Dow Chemical) | 25.25 grams |
| Triethyl citrate | 5.05 grams |
| Acetone | 833.4 grams |
| Methanol | 277.8 grams |

Eudragit L100 and ethyl cellulose are dissolved in the mixture of acetone and methanol. Subsequently, methyl citrate is added to the polymer solution. Into the Wurster column is charged 500 grams of MASL beads which are then coated with the coating mixture under conditions of 40° C., spray pressure 1 bar, and spray rate 10 grams/min. The line is rinsed with methanol and the pellets are dried for approximately twenty minutes and recovered to give a product of 90% by weight MASL beads and 10% by weight ethyl cellulose Eudragit L100 coating.

SR Matrix Beads/Tablets

Example 7

| | |
|---|---|
| Amphetamine Aspartate | 50 grams |
| Amphetamine Sulfate | 50 grams |
| Dextroamphetamine saccharate | 50 grams |
| Dextroamphetamine sulfate | 50 grams |
| Microcrystalline cellulose | 400 grams |
| Poly(ethylene oxide), Polyox WSR 303 | 1380 grams |
| Magnesium stearate | 20 grams |

All the amphetamine salts, microcrystalline cellulose, and poly(ethylene oxide) are sieved through a 60 mesh screen and loaded into a V-shaped blender with an intensifier bar. The powder mixture is blended for 15 min, with the intensifier bar on for 3 min. at the middle of the blending process. The powder blend is unloaded and screened through a 60 mesh sieve. The screened powder blend is lubricated with magnesium stearate in the V-shaped blender for 3 min. The lubricated powder blend is compacted in a roller compactor to form granules.

Example 8

| | |
|---|---|
| Amphetamine Aspartate | 50 grams |
| Amphetamine Sulfate | 50 grams |
| Dextroamphetamine saccharate | 50 grams |
| Dextroamphetamine sulfate | 50 grams |
| Microcrystalline cellulose | 1780 grams |
| Magnesium stearate | 20 grams |

All the amphetamine salts and microcrystalline cellulose are sieved through a 60 mesh screen and loaded into a V-shaped blender with an intensifier bar. The powder mixture is blended for 15 min, with the intensifier bar on for 3 min, at the middle of the blending process. The powder blend is unloaded and screened through a 60 mesh sieve. The screened powder blend is lubricated with magnesium stearate in the V-shaped blender for 3 min. The lubricated powder blend is compressed into tablets using 3/32" tooling.

Example 9

| | |
|---|---|
| Mini-tablets | 500 grams |
| Surelease | 127.7 grams |
| water | 85.1 grams |

Surelease (127.7 grams) is diluted with 85.1 grams of water. Into the Wurster column (Versa-Glatt, Glatt Air Techniques) is charged 500 grams of the mini-tablets which are then coated with the coating mixture under conditions of 60 C. inlet temperature, spray pressure 1 bar, and spray rate 6 grams/min. The line is rinsed with water and the pellets are dried for approximately twenty minutes and recovered to give a product of 94% by weight MASL minitablets and 6% by weight ethyl cellulose coating.

Example 10

| | |
|---|---|
| Mixed amphetamine salts loaded beads | 500 grams |
| Surelease (Ethyl cellulose-based dispersion, Colorcon) | 272.7 grams |
| Water | 68.2 grams |

Surelease (272.7 grams) is diluted with 68.2 grams of water. Into Wurster column (Versa-Glatt, Glatt Air Techniques) is charged 500 grams of MASL beads which are then coated with the coating mixture under conditions of 60 degree C. inlet temperature, spray pressure 1 bar, and spray rate 6 grams/min. The line is rinsed with water and the pellets are dried for approximately twenty minutes and recovered to give a product of 88% by weight MASL beads and 12% by weight ethyl cellulose coating.

The dissolution data for 8% and 12% coating levels are summarized as follows:

| | 1 hour | 2 hours | 4 hours | 6 hours | 8 hours |
|---|---|---|---|---|---|
| 8% coating | 45% | 74% | 93% | 98% | 100% |
| 12% coating | 25% | 47% | 70% | 81% | 87% |

Example 11

Background

A 2-component extended release formulation of Adderall® (mixed salts of d- and l-amphetamine) designed to produce pulse-release of medication, yields a therapeutic effect for the treatment of Attention-Deficit/Hyperactivity Disorder (ADHD) that lasts throughout the day with one morning dose. This Adderall XR™ capsule formulation is composed of 2 types of Microtrol™ beads of mixed salts of amphetamine in a 50:50 ratio within one capsule. The immediate-release beads are designed to release drug content in a time course similar to Adderall® tablets. The delayed-release beads are designed to release drug content approximately 4 hours after oral administration of the capsule. An initial formulation study with Adderall XR® 20 mg QD demonstrated comparable bioavailability and pharmacokinetic profiles to immediate-release Adderall® 10 mg BID with a 4-hour interval and concluded that Adderall XR® 20 mg QD is bioequivalent to Adderall® 10 mg BID (Michaels et al. Presented, NCDEU 2001).

Objectives

The efficacy and extended duration of action of Adderall XR® in the treatment of children with ADHD has been demonstrated in 2 previous pivotal double-blind studies: one conducted in a laboratory classroom setting (McCracken et al. Submitted), and the other in a naturalistic home and school environment (Biederman et al. Pediatrics 2002. In press). This large-scale, open-label trial has been conducted primarily to evaluate the tolerability and effectiveness of Adderall XR™ in the treatment of pediatric ADHD in the community practice setting.

Methods

Presented here are unaudited data of this prospective, open-label, 7-week study conducted at 378 sites nationwide. An 8-week extension arm was optional after completion of this initial phase See FIG. 13.

Subjects: Children aged 6 to 12 years who had a DSM-IV diagnosis of ADHD and were currently taking stable doses of immediate-release Adderall® or any methylphenidate formulation were enrolled.

Inclusion Criteria: Good physical health with normal blood pressure, pulse, and electrocardiogram (ECG); Conners Global Index Scale-Parent (CGIS-P) rating score of <_12 for boys and <_10 for girls; known responder to psychostimulant medication. Exclusion Criteria: Uncontrolled; symptomatic comorbid psychiatric disorder; IQ<80; history of seizure disorder or Tourette's; concomitant medications, such as clonidine, guanfacine, anticonvulsants, or any medications that affect blood pressure or the heart.

Measures:

Primary Efficacy: Validated CGIS-P

Figure 2:
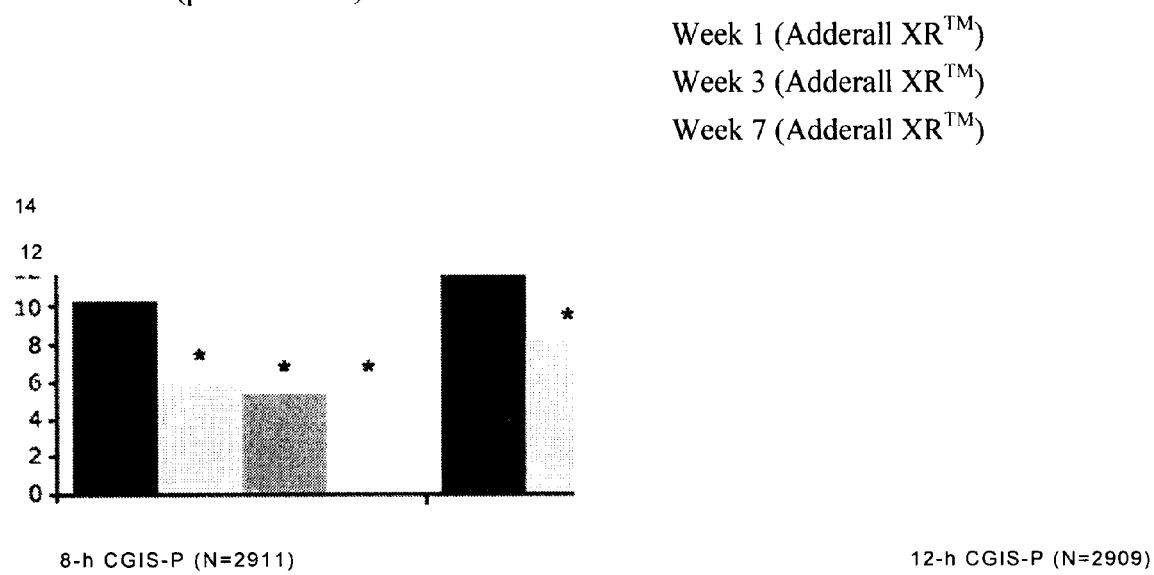
FIG. 2 shows mean CGIS-P total scores.

Baseline: 2 to 3 hours after morning dose of previous psychostimulant medication to assess degree of control of symptoms plus additional assessments at 8 and 12 hours after dose. See FIG. 2.

Figure 3:
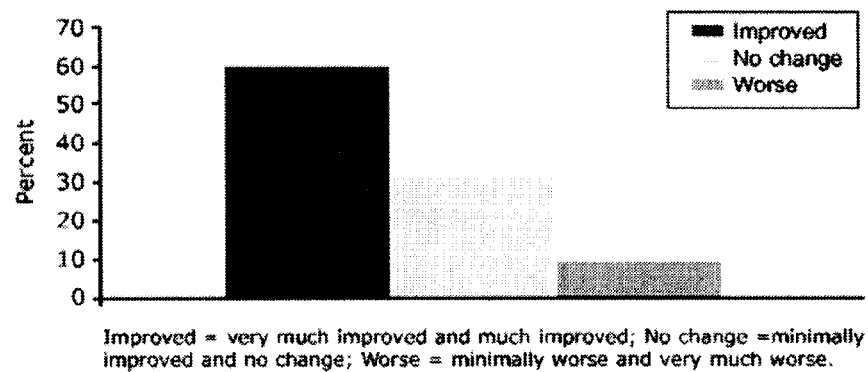
FIG. 3 shows CGI Improvement scores.

Following initiation of treatment with Adderall XR™: prior to clinic visit at weeks 1, 3, and 7; administered by same parent/caregiver at 8 hours and again at 12 hours after the morning dose of Adderall XR™. Secondary Efficacy: Clinical Global Impression Scales (CGI). Rated by the clinician. Gives a global evaluation of clinical status over time. See FIG. 3.

Subjects rated for severity at baseline while on previous psychostimulant medication. The CGI-S is a 7-point scale ranging from 1 (normal/not ill at all) to 7 (extremely ill).

Subjects rated for improvement at weeks 1, 3, and 7 by the CGI-I, a 7-point scale ranging from 1 (very much improved) to 7 (very much worse).

Primary Tolerability: Pediatric quality of life (PedsQL™)

Validated measure assessing age-specific quality-of-life markers in healthy children and those with acute and chronic health conditions.

Figure 4:
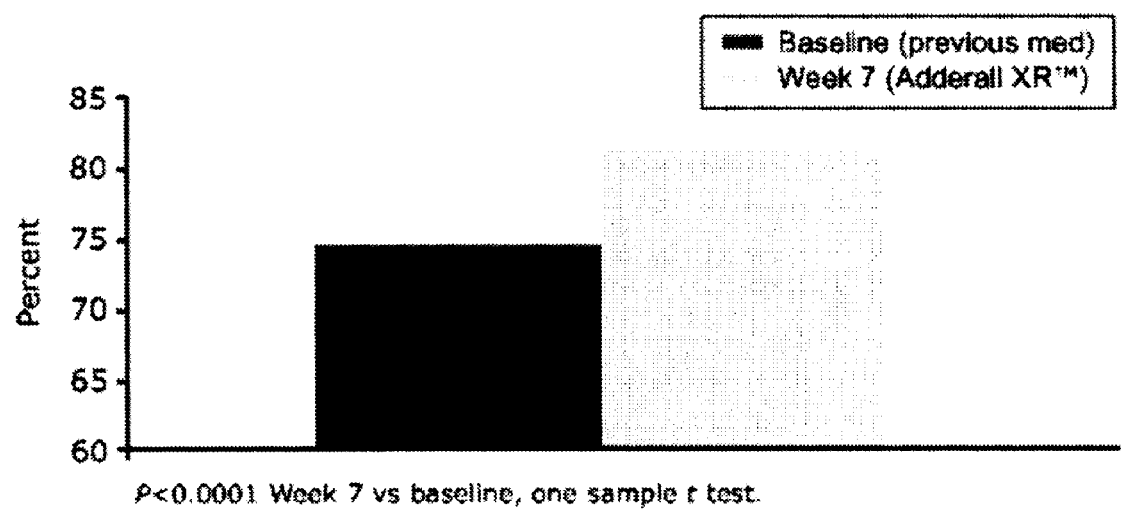
FIG. 4 shows PedsQL total scores.

Completed by parent/caregiver at baseline and end of initial phase of study (week 7). See FIG. 4.

Secondary Tolerability: Medication Satisfaction and Preference Instruments Scales allowing evaluation of the acceptability of Adderall XR™ by both the parent/caregiver and physician (separate scales for physician and parent). Satisfaction Instrument given at baseline and week 7. Preference Instrument given at week 7.

Primary Safety: Physical exam at screening (including height and weight); ECG baseline and end of study; vital signs, including pulse, blood pressure, and weight at each study visit; spontaneously reported adverse events (AEs) were recorded at each visit.

Conclusions

In children receiving stable doses of various stimulant medications, 8-and 12-hour post-dose CGIS-P scores reveal significant improvement in ADHD symptoms after conversion to Adderall XR™.

After switching to Adderall XR™, significant improvement was also apparent in CGI improvement scores and pediatric quality-of-life measures.

Figure 5:
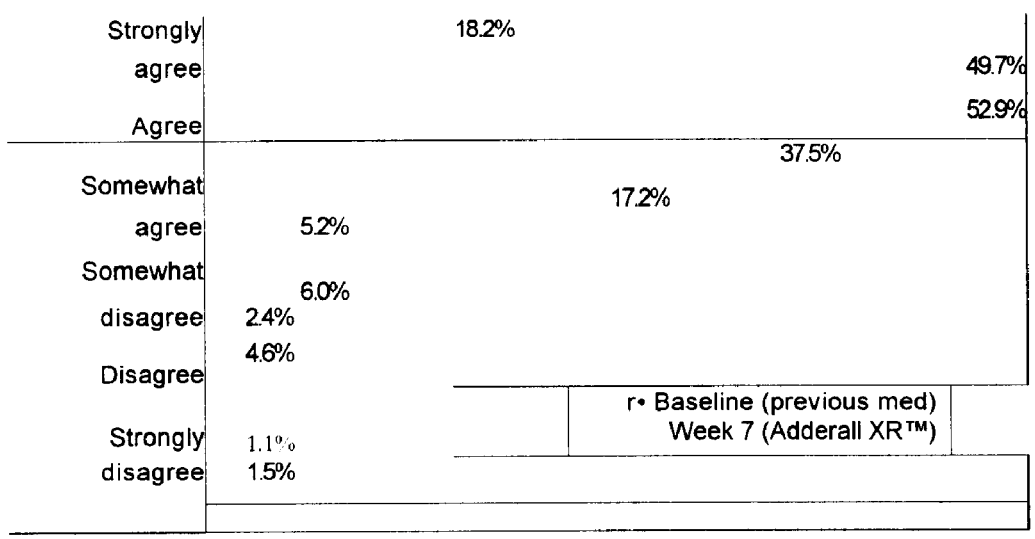
FIG. 5 shows the results of a parent satisfaction survey.
Figure 6:
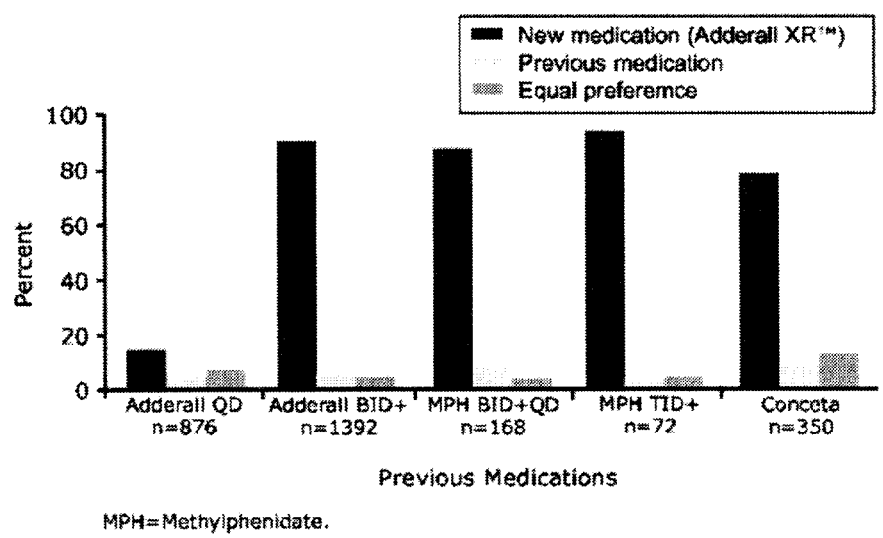
FIG. 6 shows the results of a physician preference survey.
Figure 7:
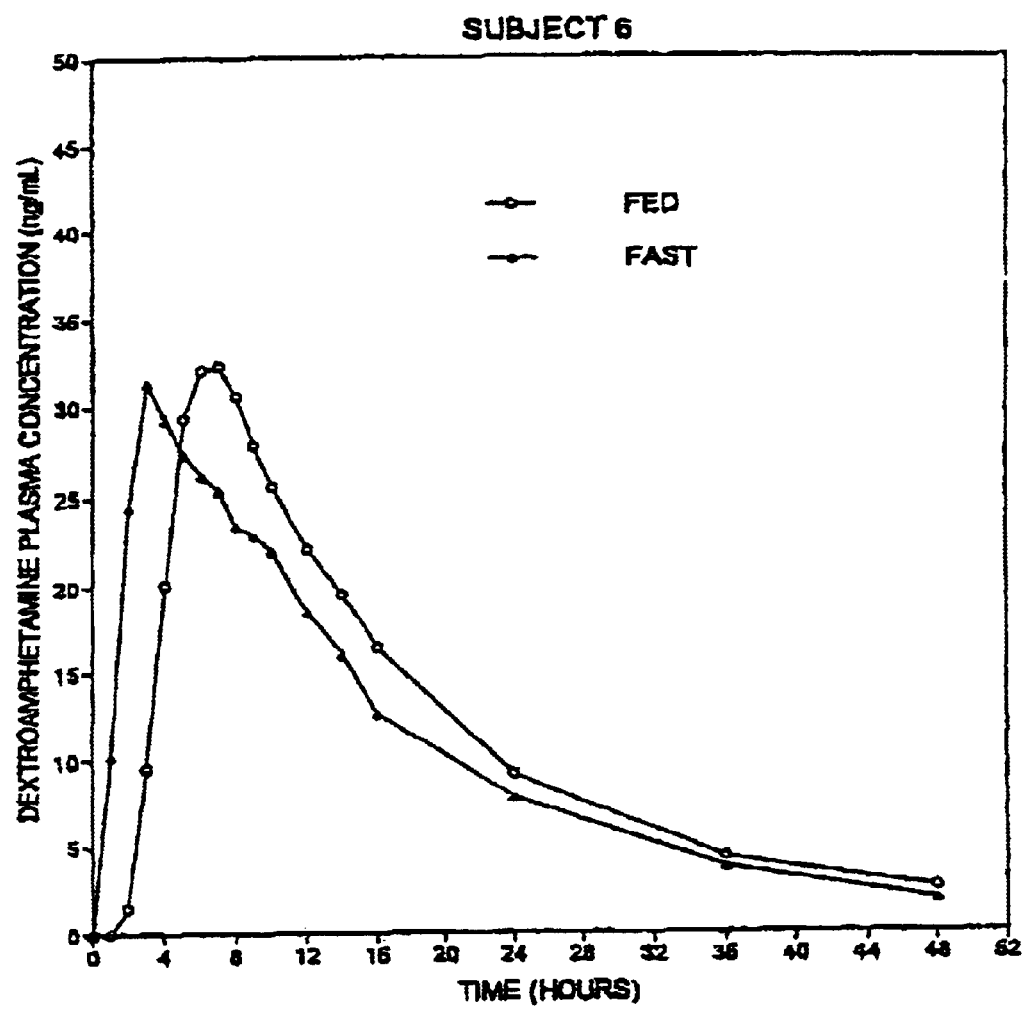
FIGS. 7–12 show plasma concentration curves for 6 individuals.
Figure 8:
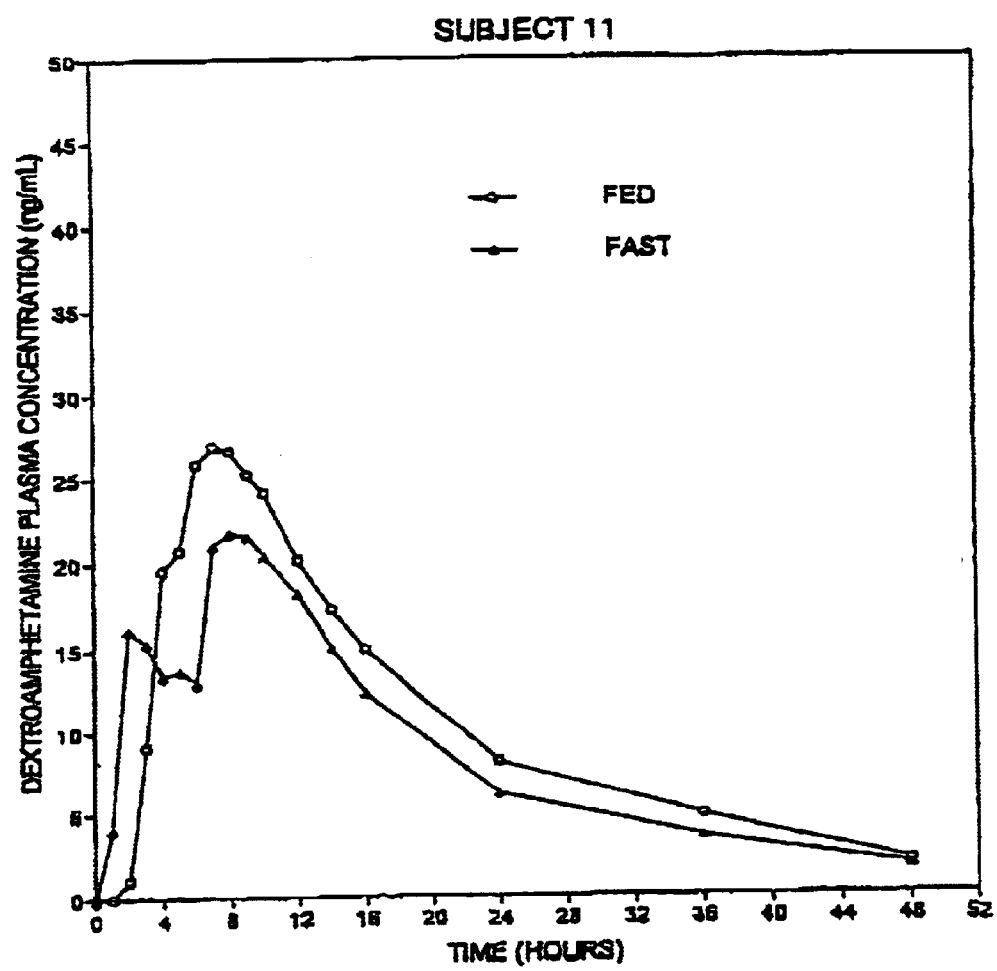
Figure 9:
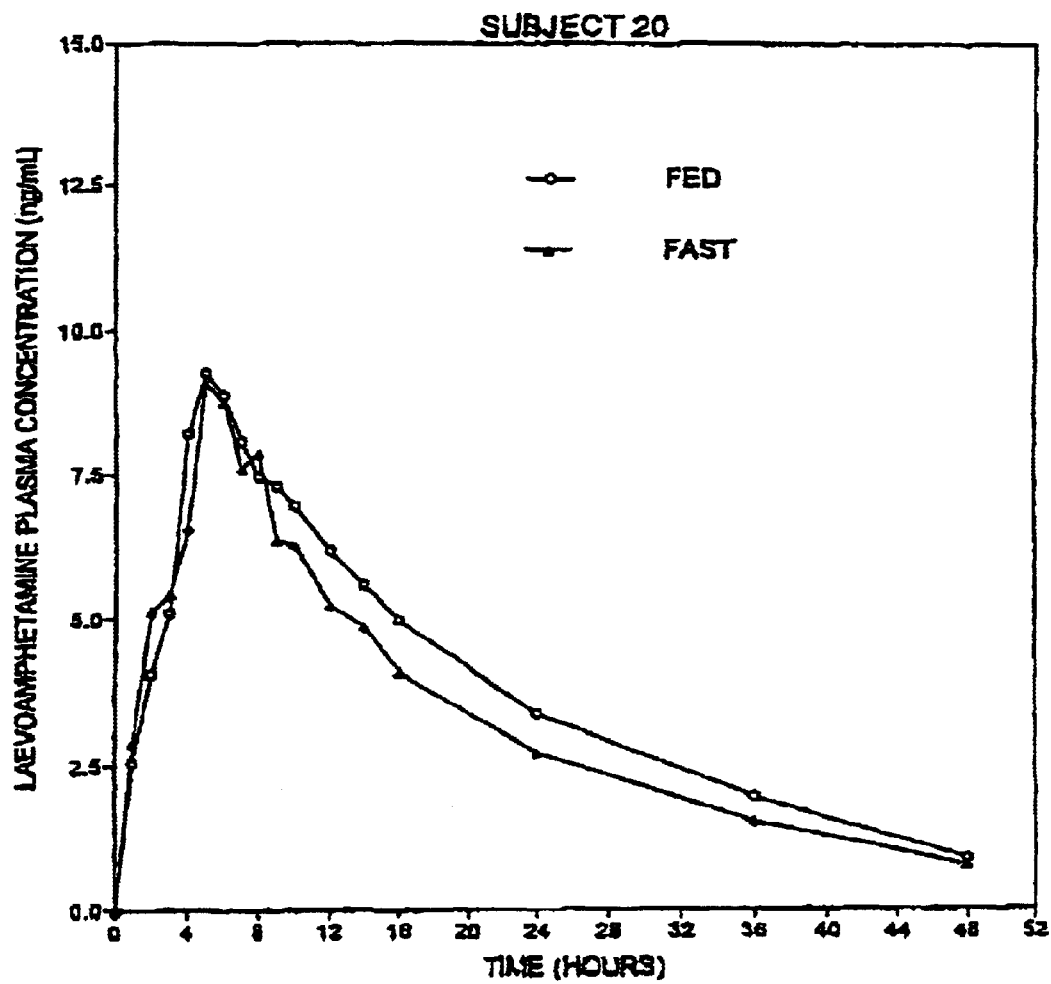
Figure 10:
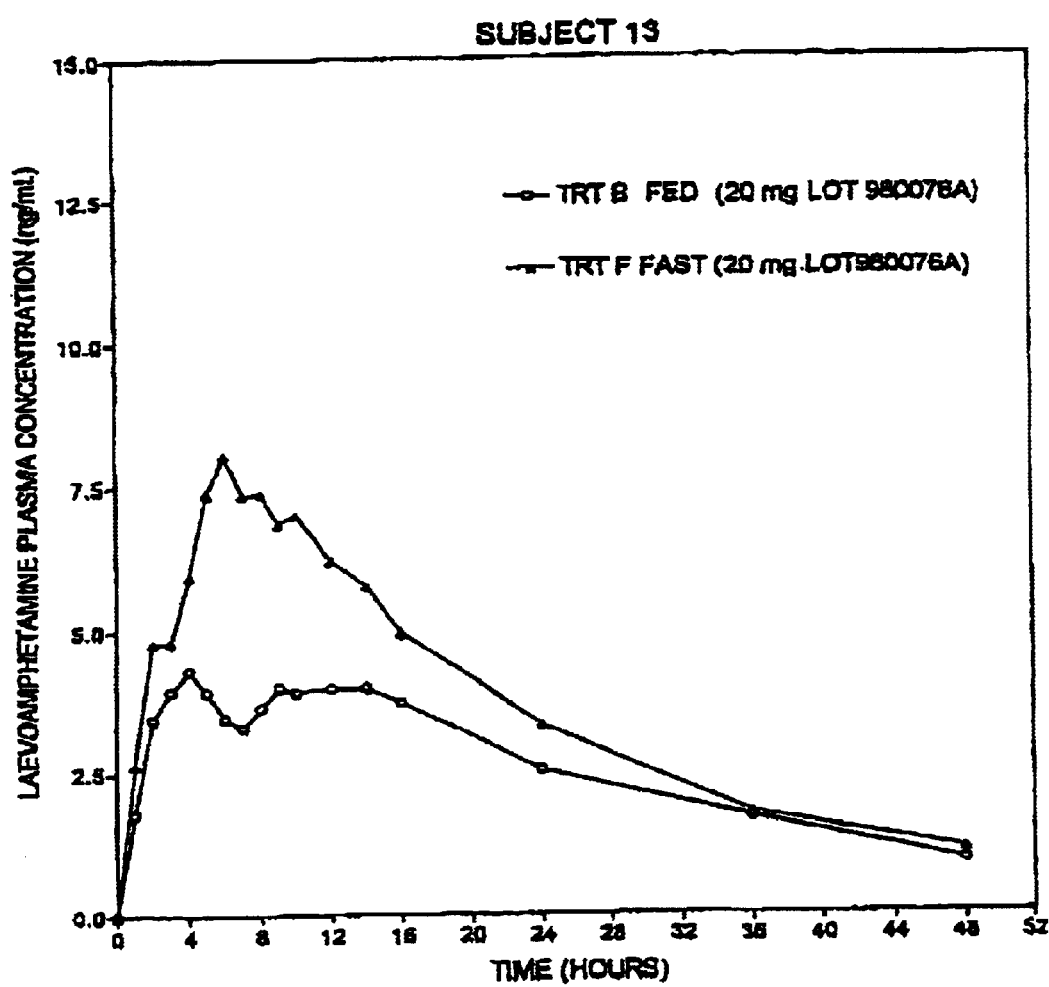
Figure 11:
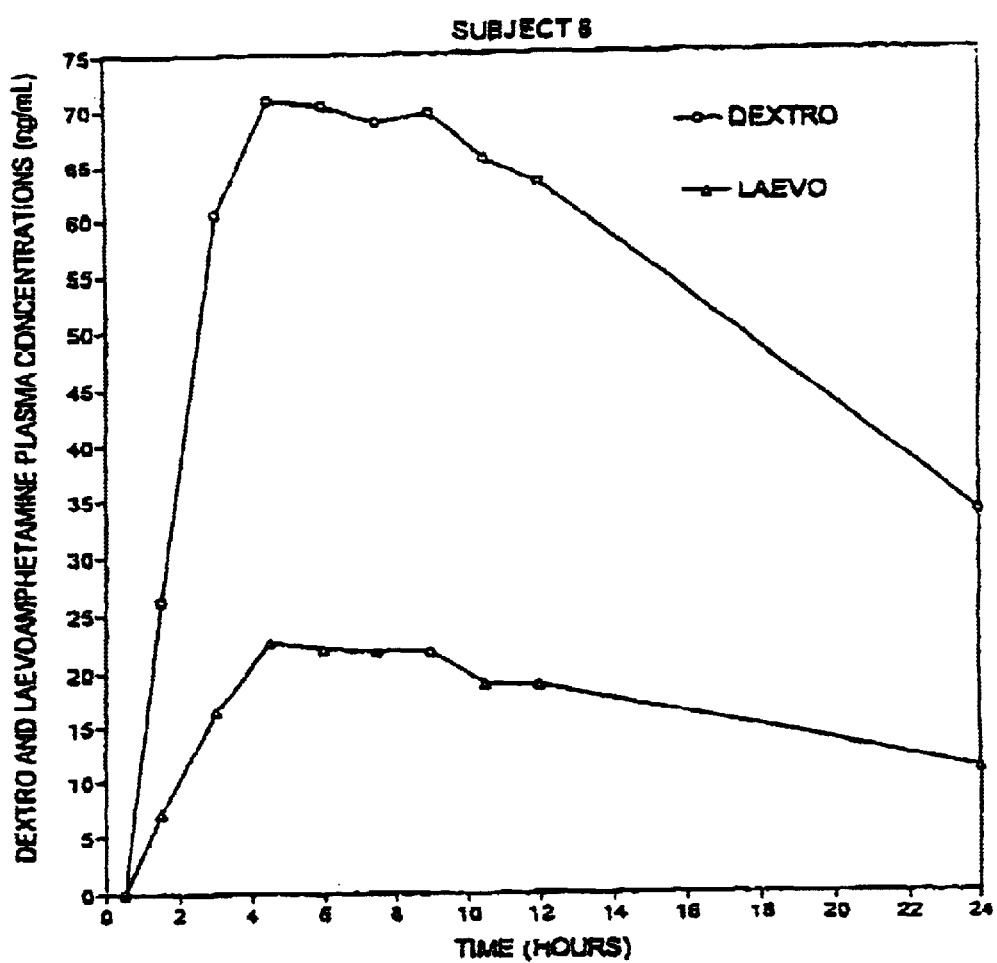
Figure 12:
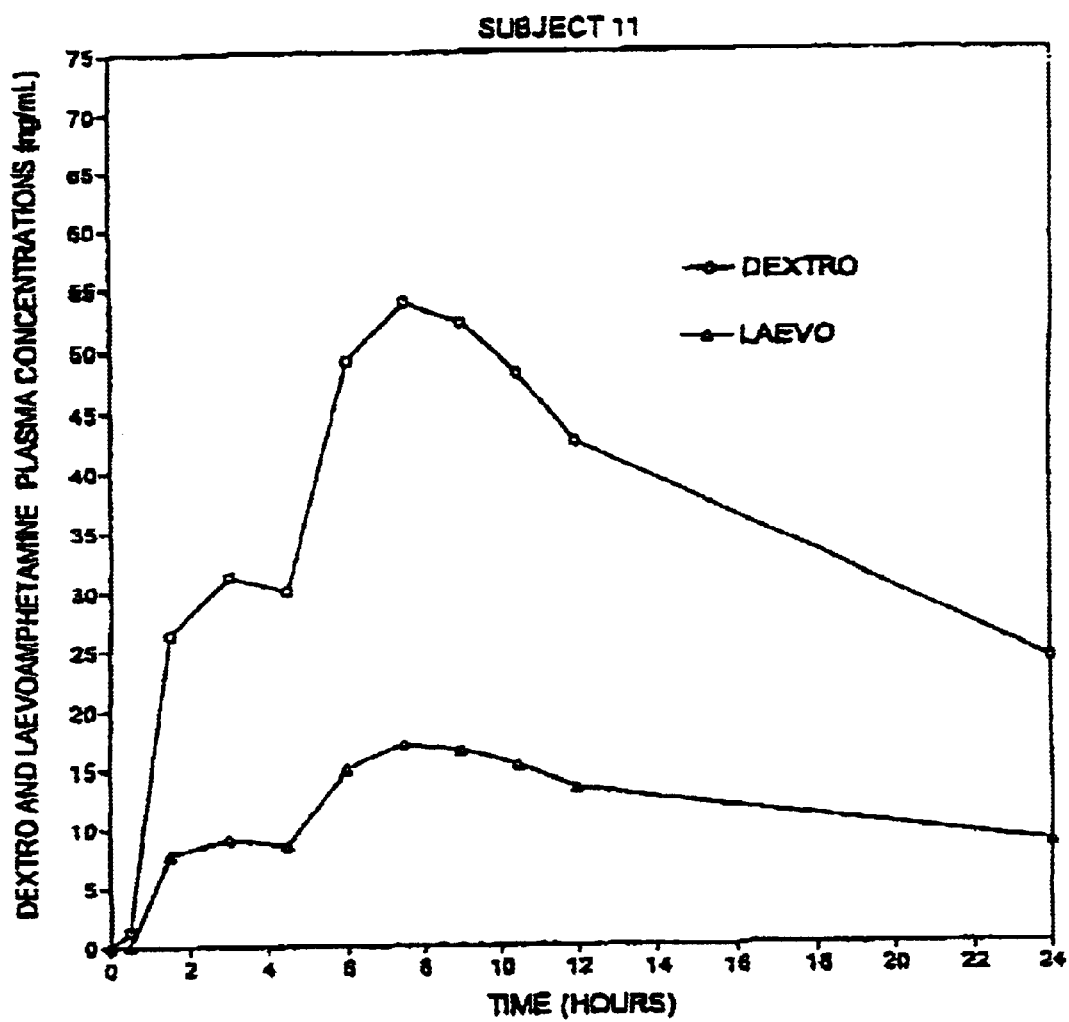

In this real-world clinical experience trial, satisfaction and preference survey results from both physicians and parents/caregivers (although not fully depicted here) also suggest significant benefit from treatment with Adderall XR™ as compared to previous medication therapy. See FIGS. 5 and 6.

These findings likely reflect (1) the established efficacy and longer duration of action of Adderall XR™, (2) elimination of the need for additional daily doses for patients in multiple-daily-dose groups (at baseline), and (3) the lower daily doses of stimulant medication treatment regimens and higher level of ADHD symptomatology previously identified with ADHD treatment regimens in the community practice setting.

The incidence of adverse events occurring during treatment was low, and the majority of AEs were mild in nature; study medication was well tolerated. Adderall XR™ is a safe and effective medication for the community practice treatment of children with ADHD, and, although patients may be showing significant benefit on other stimulant treatment regimens, additional significant benefit may be attained by switching patients to this once-daily-dosed product.

TABLE 1

Medication Conversion Paradigm

| Current Treatment | Total Daily Dose (mg) | Multiplication Factor | Adderell XR ™ Starting Dose (mg) |
|---|---|---|---|
| Adderall ® single or divided dose | 30 | ×1 | 30 |
| | 20 | ×1 | 20 |
| | 10 | ×1 | 10 |
| Concerta ™ | 54 | ×0.55 | 30 |
| | 36 | ×0.55 | 20 |
| | 18 | ×0.55 | 10 |
| Methlphenidate (immediate and sustained release, other than) Concerta ™ | Current total daily dose of methylphenidate | ×0.50, then rounded to next lowest 10-mg increment of Adderall XR ™ | 10, 20, or 30 |

Note:
Patients who required a 40-mg starting dose of Adderall XR ™ received two 20-mg capsules QD.

Results

Of the 2968 subjects who received study medication, 2911 (98%) had at least one post-baseline CGIS-P total score available for efficacy analysis. These subjects make up the intent-to-treat (ITT) population (Table 2).

TABLE 2

Demographic and Baseline Information

| Subject Population | All Participants (N = 2968) | ITT Subjects (n = 2911) |
|---|---|---|
| Aye (y), mean ± SD | 9.5 ± 1.8 | 9.5 ± 1.8 |
| Gender | 76% male | 76% male |
| Race | | |
| White | 88.0% | 88.0% |
| Black | 6.7% | 6.7% |
| Hispanic | 3.5% | 3.4% |
| Other | 1.8% | 1.9% |
| Diagnosis | | |
| Combined | 2072 (70.2%) | 2034 (70.2%) |
| Inattentive | 682 (23.1%) | 669 (23.1%) |
| Hyperactive | 197 (6.7%) | 193 (6.7%) |
| Comorbidity | | |
| Oppositional defiant | 109 (3.7%) | 103 (3.5%) |
| Conduct disorder | 16 (0.5%) | 16 (0.5%) |
| Anxiety | 83 (2.8%) | 83 (2.9%) |
| Depression | 93 (3.1%) | 91 (3.1%) |
| Obsessive-compulsive disorder | 42 (1.4%) | 41 (1.4%) |
| Other | 78 (2.6%) | 76 (2.6%) |

Mean CGIS-P baseline score at 2 to 3 hours after morning dose of previous medication = 5.9.

Example 12

Individual patients were treated with ADDERALL XR®, 20 mg. Subjects received either one single dose administered with food or one single dose administered following a 10-hour overnight fast through continued fast 3.5 hours post dosing. A sampling of individuals' curves is given in FIGS. 7-12. The mean plasma concentration profile of FIG. 1 was obtained from averaging such individuals' curves.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or poly(ethylene oxide) effective to achieve continuous sustained release of said amphetamines and/or salt(s) to provide a mean plasma concentration profile in human ADHD patients which is substantially the same as the dextroamphetamine XR profile and/or the levoamphetamine XR profile of FIG. 1 over the course of the first twelve hours after administration, for a 20 mg total dose, or to provide a profile directly proportional to said XR profile(s) for a total dose other than 20 mg.

2. The composition of claim 1, comprising a mixture of dextroamphetamine sulfate, dextroamphetamine saccharate, amphetamine aspartate and amphetamine sulfate.

3. The pharmaceutical composition of claim 2, comprising equal amounts by weight of dextroamphetamine sulfate, dextroamphetamine saccharate, amphetamine aspartate and amphetamine sulfate.

4. The pharmaceutical composition of claim 1, wherein said amphetamines and/or salt(s) are provided in a core which is coated with a coating comprising a pharmaceutically acceptable water-insoluble film-former providing sustained release or other polymer providing sustained release.

5. The pharmaceutical composition of claim 4, wherein the coating further comprises a dissolution regulating agent.

6. A method for treating attention deficit hyperactivity disorder which comprises administering to a human patient in need thereof a pharmaceutical composition of claim 1.

7. A pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or poly(ethylene oxide) effective to achieve continuous sustained release of said amphetamines and/or salts to provide a mean plasma concentration profile in human ADHD patients which has substantially the same initial slope as the dextroamphetamine XR profile and/or the levoamphetamine XR profile of FIG. 1 from 2 hours to 4 hours after administration, for a 20 mg total dose, or respective initial slope(s) from 2 hours to 4 hours after administration directly proportional to that of said XR profile(s) for a total dose other than 20 mg.

8. A method for treating attention deficit hyperactivity disorder which comprises administering to a human patient in need thereof a pharmaceutical composition of claim 7.

9. A pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or poly(ethylene oxide) effective to achieve continuous sustained release of said amphetamines and/or salt(s) to provide a mean plasma concentration profile in human ADHD patients which has an initial slope from 2 hours to 4 hours after administration of about 3.7 to about 11.4 ng/(mL hr) for dextroamphetamines and/or about 1.4 to about 3 ng/(mL hr) for levoamphetamines, all at a total amphetamine dose of 20 mg, or respective initial slope(s) from 2 hours to 4 hours after administration directly proportional thereto for a total dose other than 20 mg.

10. A method for treating attention deficit hyperactivity disorder which comprises administering to a human patient in need thereof a pharmaceutical composition of claim 9.

11. A pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a polly(meth)acrylate, microcrystalline cellulose or poly(ethylene oxide) effective to achieve continuous sustained release of said a amphetamines and/or salt(s) to provide a means plasma concentration profile in human ADHD patients which has an initial slope from 2 hours to 4 hours after administration of about 4 to about 8 ng/(mL hr) for dextroamphetamines and/or about 1.5 to about 2.2 ng/(mL hr) for levoamphetamines, all at a total amphetamine dose of 20 mg, or respective initial slope(s) from 2 hours to 4 hours after administration directly proportional thereto for a total dose other than 20 mg.

12. A pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or poly(ethylene oxide) effective to achieve continuous sustained release of said amphetamine and/or salt(s) to provide a mean plasma concentration profile in human ADHD patients which has an AUC of 556.6 mg hr/mL±20% and a $C_{max}$ of 28.0 ng/mL±20% for dextroamphetamine and/or an AUC of 205.1 ng hr/mL±20% and a $C_{max}$ of 8.7 ng/mL±20% for levoamphetamine, for a 20 mg total dose, or respective AUC and Cmax values directly proportional thereto for a total dose other than 20 mg.

13. A method for treating attention deficit hyperactivity disorder which comprises administering to a human patient in need thereof a pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or poly(ethylene oxide) effective to achieve sustained continuous release of said amphetamine and/or salt(s) to provide a mean plasma concentration profile in human ADHD patients which has an AUC of 556.6 mg hr/mL±20% and a $C_{max}$ of 28.0 ng/mL±20% for dextroamphetamine and/or an AUC of 205.1 ng hr/mL±20% and a $C_{max}$ of 8.7 ng/mL±20% for levoamphetamine, for a 20 mg total dose, or respective AUC and Cmax values directly proportional thereto for a total dose other than 20 mg.

14. A pharmaceutical composition comprising a mixture of dextro- and levo-amphetamine and/or salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or polyethylene oxide) effective to achieve about a first order sustained dissolution release of said amphetamines and/or salt(s), which has an AUC of 556.6 mg hr/mL±20% and a $C_{max}$ of 28.0 ng/mL±20% for dextroamphetamine and/or an AUC of 205.1 ng hr/mL±20% and a $C_{max}$ of 8.7 mg/mL±20% for 1 levoamphetamine, for a 20 mg total dose, or respective AUC and Cmax values directly proportional thereto for a total dose other than 20 mg.

15. A pharmaceutical composition comprising a mixture of dextro- and levo-amphetamine salt(s) thereof and a sustained release coating or matrix which comprises an amount of polyvinyl acetate, cellulose acetate, cellulose acetate butyrate, cellulose acetate propionate, ethyl cellulose, a fatty acid, a fatty acid ester, an alkyl alcohol, a wax, zein (prolamine from corn), a poly(meth)acrylate, microcrystalline cellulose or poly(ethylene oxide) effective to achieve a single sustained dissolution release of said amphetamines and/or salt(s), which has an AUC of 556.6 mg hr/mL±20% and a $C_{max}$ of 28.0 mg/mL±20% for dextroamphetamine and/or an AUC of 205.1 ng hr/mL±20% and a $C_{max}$ of 8.7 ng/mL±20% for levoamphetamine, for a 20 mg total dose, or respective AUC and Cmax values directly proportional thereto for a total dose other than 20 mg.

16. The pharmaceutical composition of claim 1, 16, 17, 18, 21, 31 or 32 comprising a sustained release matrix.

17. The pharmaceutical composition of claim 16 wherein said sustained release matrix comprises ethyl cellulose.

18. A method for treating attention deficit hyperactivity disorder which comprises administering to a human patient in need thereof a pharmaceutical composition of claim 17.

19. The pharmaceutical composition of claim 1, 7, 9, 11, 12, 14, or 15 comprising a mixture of dextroamphetamine sulfate, dextroamphetamine saccharate, amphetamine aspartate and amphetamine sulfate.

20. The composition of claim 19 wherein said coating or matrix comprises ethyl cellulose.

21. The pharmaceutical composition of claim 1, 7, 9, 11, 12, 14 or 15 wherein said formulation comprises said amphetamines and/or salt(s) in a core which is coated with a sustained release coating.

22. The pharmaceutical composition of claim 21 wherein said coating comprises ethyl cellulose.

23. The pharmaceutical composition of claim 1, 7, 9, 11, 12, 14 or 15 wherein said formulation comprises a core coated with a coating comprising said amphetamines and/or salt(s), which amphetamine coated core is coated with a sustained release coating comprising ethyl cellulose.

24. The pharmaceutical composition of claim 1, 7, 9, 11, 12, 14 or 15 wherein said formulation comprises a core coated with a coating comprising said amphetamines and/or salt(s), which amphetamine coated core is coated with a sustained release coating comprising a water insoluble polymer.

25. The pharmaceutical composition of claim 1, 7, 9, 11, 12, 14 or 15 wherein the dissolution release profile of said amphetamines and/or salt(s) is first order.

26. The pharmaceutical composition of claim 25 wherein said release profile is determined in a dissolution profile test.

27. The pharmaceutical composition of claim 1, 7, 9, 11, 12, 14 or 15 wherein said sustained release coating or matrix comprises polyvinyl acetate, cellulose acetate, cellulose acetate butyrate, cellulose acetate propionate, ethyl cellulose, microcrystalline cellulose or poly(ethylene oxide).

28. The pharmaceutical of claim 1, 7, 9, 11, 12, 14 or 15 wherein said coating or matrix comprises polyvinyl acetate, cellulose acetate, cellulose acetate butyrate, cellulose acetate propionate or ethyl cellulose.

29. The pharmaceutical composition of claim 1, 7, 9, 11, 12, 14 or 15 comprising a sustained release coating.

30. The pharmaceutical composition of claim 29 wherein said sustained release coating comprises ethyl cellulose.

31. A pharmaceutical composition of claim 1, 9, 11, 12, 14 or 15 wherein said sustained release coating or matrix has pH independent dissolution release.

32. A pharmaceutical composition of claim 9, 11, 12, 13, 22, 14 or 15 wherein said stated numerical value range is achieved for dextroamphetamine.

33. A pharmaceutical composition of claim 9, 11, 12, 13, 22, 14 or 15 wherein said stated numerical value range is achieved for levoamphetamine.

34. A pharmaceutical composition of claim 9, 11, 12, 13, 22, 14 or 15 wherein said stated numerical value range is achieved for both dextroamphetamine and levoamphetamine.

35. A pharmaceutical composition comprising a mixture of dextro- and levo-amphetamine and/or salt(s) thereof and a sustained release coating which comprises an amount of ethyl cellulose effective to achieve continuous sustained release of said amphetamine and/or salt(s) to provide a mean plasma concentration profile in human ADHD patients which has an AUC of 556.6 mg hr/mL±20% and a $C_{max}$ of 28.0 ng/mL±20% for dextroamphetamine and/or an AUC of 205.1 ng hr/mL±20% and a $C_{max}$ of 8.7 ng/mL±20% for levoamphetamine, for a 20 mg total dose, or respective AUC and Cmax values directly proportional thereto for a total dose other than 20 mg.

36. The pharmaceutical composition of claim 35 comprising a mixture of dextroamphetamine sulfate, dextroamphetamine saccharate, amphetamine aspartate and amphetamine sulfate.

37. The pharmaceutical composition of claim 36 wherein said formulation comprises amphetamine coated cores, coated with a coating comprising ethyl cellulose.

* * * * *